United States Patent [19]

Grollier

[11] Patent Number: 4,804,531

[45] Date of Patent: Feb. 14, 1989

[54] COSMETIC SCREENING COMPOSITION CONTAINING A UV SCREEN IN COMBINATION WITH A POLYMER OBTAINED BY BLOCK POLYMERIZATION IN EMULSION AND ITS USE FOR THE PROTECTION OF THE HUMAN EPIDERMIS AGAINST ULTRAVIOLET RADIATIONS

[75] Inventor: Jean F. Grollier, Paris, France

[73] Assignee: L'Oreal, Paris, France

[21] Appl. No.: 821,978

[22] Filed: Jan. 24, 1986

[30] Foreign Application Priority Data

Jan. 28, 1985 [LU] Luxembourg .............................. 85746

[51] Int. Cl.$^4$ .......................... A61K 7/40; A61K 7/42; A61K 7/44; A61K 9/12
[52] U.S. Cl. ........................................ 424/47; 424/59; 424/60; 514/937; 514/938; 514/944; 514/969; 514/972
[58] Field of Search .............................. 424/59, 60, 47

[56] References Cited

U.S. PATENT DOCUMENTS

| | | | |
|---|---|---|---|
| 2,628,205 | 2/1953 | Shoemaker | 424/83 |
| 4,522,808 | 6/1985 | Jacquet et al. | 424/78 |
| 4,524,061 | 6/1985 | Cho et al. | 424/78 |
| 4,535,130 | 8/1985 | Favie et al. | 424/78 |
| 4,673,571 | 6/1987 | Mahieu et al. | 424/60 |

FOREIGN PATENT DOCUMENTS

| | | | |
|---|---|---|---|
| 0073529 | 6/1980 | European Pat. Off. | 424/78 |
| 0055857 | 12/1981 | European Pat. Off. | 424/59 |
| 2723682 | 4/1978 | Fed. Rep. of Germany | 424/83 |
| 2333493 | 12/1976 | France | 424/60 |
| 2431290 | 7/1979 | France | 424/59 |
| 1557580 | 12/1976 | United Kingdom | 424/59 |
| 2002652 | 2/1979 | United Kingdom | 424/83 |
| 2028131 | 6/1979 | United Kingdom | 424/59 |

*Primary Examiner*—Dale R. Ore
*Attorney, Agent, or Firm*—Cushman, Darby & Cushman

[57] ABSTRACT

Cosmetic screening composition containing a UV screen in combination with a polymer obtained by block polymerization in emulsion and its use for the protection of the human epidermis against ultraviolet radiations.

15 Claims, No Drawings

COSMETIC SCREENING COMPOSITION CONTAINING A UV SCREEN IN COMBINATION WITH A POLYMER OBTAINED BY BLOCK POLYMERIZATION IN EMULSION AND ITS USE FOR THE PROTECTION OF THE HUMAN EPIDERMIS AGAINST ULTRAVIOLET RADIATIONS

The invention relates to a cosmetic composition screening the UV rays and containing at least one UV screen in combination with an aqueous dispersion of particles of a water-insoluble polymer comprising (a) an ionic polymer forming a core, containing ionizable acid groups which make the core capable of being swollen by at least partial neutralization with a volatile base and (b) a polymer forming a sheath at least partially encapsulating the core and permeable to the volatile base, the outer sheath having a glass transition temperature below 50° C. and the particles being film-forming, which is obtained by a process of block polymerization in emulsion, in a cosmetically acceptable vehicle.

The effect of the polymer is to increase the protection index of the screening composition.

The present invention relates to a cosmetic composition screening ultraviolet radiations, containing a UV screen and a polymer obtained by block polymerization in emulsion, the effect of which is to increase the protection index of the said screening composition, and the use of the said composition to protect the human epidermis against ultraviolet radiations.

It is known that light radiations of wavelengths between 280 and 320 nm, known by the name of UV.B, produce erythemas and cutaneous burns whose severity increases rapidly with the duration of exposure.

As a result, agents which screen these radiations and whose effectiveness is expressed by a sun protection factor, which is conventionally called a protection index or PI, are added to sunscreen preparations.

$$PI = \frac{\text{Irradiation time required to reach the erythematogenic threshold with a UV screen}}{\text{Irradiation time required to reach the erythematogenic threshold without a UV screen}}$$

It is known, furthermore, that in some cases the agents which screen the UV.B rays can give rise to adverse secondary effects, and that it is in the cosmetologist's interest to obtain the required protection index with the lowest possible quantity of screening agent in the composition.

Moreover, it is difficult to obtain, using means known hitherto, a cosmetic screening composition which, in addition to a high protection index, does not allow a whitish film, hardly appreciated by the users, to remain on the skin after an application, which is not sticky to the touch and which has good chemical and photochemical stability.

Surprisingly, the applicant has found that by adding to a cosmetically acceptable vehicle containing at least one oil-soluble and/or water-soluble agent screening the ultraviolet radiations, an aqueous dispersion of particles of a water-insoluble polymer defined hereinafter, a cosmetic composition is obtained which screens the UV.B rays, and which has the combination of the above required characteristics and more especially an increased protection index, which advantageously enables the content of the screening agent in the earlier compositions to be reduced.

The subject of the present invention is consequently a cosmetic composition screening the UV rays, containing, in a cosmetically acceptable vehicle, at least one oil-soluble and/or water-soluble agent screening the ultraviolet radiations and at least one aqueous dispersion of particles of a water-soluble polymer, comprising:

(a) an ionic polymer forming a core, containing ionizable acid groups which make the core capable of being swollen by at least partial neutralization with a volatile base and, (b) a polymer forming a sheath at least partly encapsulating the core and permeable to the volatile base, the outer sheath having a glass transition temperature below 50° C. and the particles being filmforming, the said aqueous dispersion of polymer being obtained by the process of block polymerization in emulsion described in Patent Application EP No. 73,529, where it is employed especially as a thickening agent for aqueous coating compositions.

In accordance with the process described in said EP No. 73,529 the water-insoluble polymer of the present invention is prepared by sequential emulsion polymerization in an aqueous medium so as to form an aqueous dispersion of water-insoluble hetero-polymer particles comprising (1) an ionic core polymer containing ionizable acid group making the core swellable by the action of a swelling agent consisting essentially of an aqueous liquid or a gaseous medium containing a volatile base to at least partially neutralize (to a pH of at least about 6 to 10) the acid core polymer and thereby to cause swelling by hydration thereof and (2) a sheath polymer on the core, the sheath being permeable to the swelling agent. The composition of the sheath polymer in the preferred embodiments is such as to render it permeable at ambient temperature (e.g. at room temperature of about 20° C.) or at moderately elevated temperature, such as up to about 80° C. to about 120° C., to a volatile neutralizing base, such as ammonia, or an organic neutralizing base, such as a lower aliphatic amine, e.g. triethylamine, diethanolamines, triethanolamine, morpholine and the like, to allow swelling of the acid core polymer by such volatile bases in aqueous or gaseous media.

Another subject of the present invention is a process for protecting the human epidermis against the UV rays, consisting in applying on the skin an effective quantity of the cosmetic screening composition defined above.

The cosmetic screening composition according to the invention contains at least one aqueous dispersion of an acrylic heteropolymer described in the abovementioned Patent Application EP No. 73,529 and more particularly an aqueous dispersion of a water-insoluble acrylic heteropolymer prepared according to the process of block polymerization in emulsion, described in the said application and such that the shear polymer has a glass transition temperature of −40° to +23° C. and encapsulates the core polymer to an extent of over 50% and preferably over 85%, and that the volatile base required to swell the core is in a sufficient quantity to obtain a pH of at least 6 and preferably 9–10.

The preferred monomers used in the core polymer are acrylic and/or methacrylic acid in a proportion of at least 15% by weight and a polyunsaturated crosslinking monomer in a proportion of 0.1% to 3% relative to the total weight of the core monomers, where the acrylic and/or methacrylic acid present in the sheath monomer must not exceed 10% of the total weight of the sheath monomer and must be less than one third of its proportion in the core monomer. The size of the core/sheath particles before swelling by neutralization is between 0.07 and 4.5 microns, preferably between 0.1 and 3.5 and advantageously between 0.2 and 2 microns.

The core polymer preferably comprises, as a polyunsaturated crosslinking monomer, ethylene glycol di(meth)acrylate, allyl (meth)acrylate, 1,3-butanediol di(meth)acrylate, diethylene glycol di(meth)acrylate, trimethylolpropane trimethacrylate or divinylbenzene.

Preferably, the polymer sold under the name "Ropaque OP 42" by the company Rohm and Haas is used in the cosmetic screening composition according to the invention.

The polymer is present in the cosmetic screening composition according to the invention in a proportion of 0.1% to 10% by weight of active substance relative to the total weight of the composition, and preferably in a proportion of 0.5% to 5% by weight, and the agents screening the ultraviolet radiations are present at a total concentration of 1% to 20% by weight and preferably from 2 to 15% by weight relative to the total weight of the composition.

Among the known screens which can be used in the cosmetic screening composition according to the invention there may be mentioned the UV-A and UV-B screens such as, for example:

benzylidenecamphors such as:
3-benzylidene-d,l-camphor
3-(4'-methylbenzylidene)-d,l-camphor, sold under the trademark Eusolex 6300
para-substituted 3-benzylidenecamphors, described and prepared in French Pat. Nos. 2,383,904, 2,402,647 and 2,421,878
sulphonamide derivatives of 3-benzylidenecamphor which are described and prepared in Belgian Pat. No. 897,241 of the applicant
p-benzylidenecamphor derivatives such as the 3-p-oxybenzylidene-2-bornanones described and prepared in Belgian Pat. No. 877,596 of the applicant, and other benzylidenecamphor derivatives such as those described and prepared in French Pat. Nos. 2,199,971, 2,236,515 and 2,282,426 of the applicant and more particularly 4-[(2-oxo-3-bornylidene)methyl]phenyltrimethylammonium methyl sulphate and salts of 4-(2-oxo-3-bornylidenemethyl)benzenesulphonic acid and 2-methyl-5-(2-oxo-3-bornylidenemethyl)benzenesulphonic acid,
3-cinnamylidenecamphor
1,4-dicamphormethylidenebenzenes and camphormethylidenecinnamates described and prepared in Belgian Pat. No. 897,051 of the applicant;
p-aminobenzoic acid, its esters and derivatives such as:
ethyl p-aminobenzoate, sold under the trademark Benzocaine
isopropyl p-aminobenzoate
isobutyl p-aminobenzoate, sold under the trademark Cycloform
glyceryl p-aminobenzoate, sold under the trademark Escalol 106
allantoin p-aminobenzoate, sold under the trademark Alpaba
ethyl N-ethoxy-p-aminobenzoate, sold under the name SC 9155
ethyl N-(2-hydroxypropyl)-p-aminobenzoate and ethyl N,N-bis(2-hydroxypropyl)-p-aminobenzoate, which are sold under the trademark Amerscreen P
ethyl 4-(dimethylamino)benzoate
amyl 4-(dimethylamino)benzoate or "Padimate" according to the common international nomenclature, sold under the trademark Escalot 506
2-ethylhexyl 4-(dimethylamino)benzoate, sold under the trademark Escalol 507
3,3,5-trimethylcyclohexyl 2-acetamidobenzoate;
anthranilates such as:
menthyl anthranilate
trimethylcyclohexyl N-acetylanthranilate;
cinnamates such as:
octyl cinnamate, sold under the trademark Prosolal S8
ethyl α-cyano-β-phenylcinnamate, sold under the trademark Uvinul N 35
2-ethylhexyl α-cyano-β-phenylcinnamate, sold under the trademark Uvinul N 539
α-cyano-β-p-methoxycinnamic acid and its hexyl ester
2-ethylhexyl p-methoxycinnamate, sold under the trademarks Parsol MCX and Néo Héliopan AV
amyl and isoamyl p-methoxycinnamate, sold under the trademark Néo Héliopan E 1000
propyl p-methoxycinnamate
cyclohexyl p-methoxycinnamate
2-ethoxyethyl p-methoxycinnamate or "Cinoxate" according to the common internation nomenclature, sold under the trademark Giv-Tan F
potassium cinnamate
salts of p-methoxycinnamic acid, such as the sodium, potassium and diethanolamine salts;
salicylates such as:
2-ethylhexyl salicylate
4-isopropylbenzyl salicylate benzyl salicylate
manthyl and homomenthyl salicylates, sold, respectively, under the trademarks Contrasol and Filtrasol A
potassium, sodium and triethanolamine salicylates;
certain benzoxazole derivatives such as:
2-(p-toluene)benzoxazole
5-methyl-2-phenylbenzoxazole, sold under the trademark Witisol;
other compounds such as:
5-(3,3-dimethyl-2-norbornylidene)-3-penten-2-one, sold under the trademark Prosolal S9
ethyl urocanate
the trioleate of 3,4-dihydroxy-5-[(3,4,5-trihydroxybenzoyl)oxy]benzoic acid, sold under the trademark Solprotex 1
sodium 3,4-dimethoxyphenylglyoxylate
2-phenylbenzimidazole-5-sulphonic acid and its salts;
benzophenone derivatives such as:
2-hydroxy-4-methoxybenzophenone or "oxybenzone", sold under the trademarks Spectra-Sorb UV 9, Uvinul M 40 and Eusolex 4360
2,2'-dihydroxy-4-methoxybenzophenone or "dioxybenzone", sold under the trademark Cyasorb UV 24
2,4-dihydroxybenzophenone, sold under the trademark Uvinul 400
2,2',4,4'-tetrahydroxybenzophenone, sold under the trademark Uvinul D 50
2,2'-dihyroxy-4,4'-dimethoxybenzophenone, sold under the trademark Uvinul D 49

2-hydroxy-4-methoxy-4'-methylbenzophenone or "mexenone", sold under the trademark Uvistat 2211

2-hydroxy-4-(n-octyloxy)benzophenone or "octobenzone", sold under the trademark Cyasorb UV 531

4-phenylbenzophenone, sold under the trademark Eusolex 3490

2-ethylhexyl 2-(4-phenylbenzoyl)benzoate, sold under the trademark Eusolex 3573

2-hydroxy-4-methoxybenzophenone-5-sulphonic acid and its sodium salt or "Sulisobenzone" and "sodium Sulisobenzone", sold under the trademark Uvinul MS 40;

dibenzoylmethane derivatives such as:

4-isopropyldibenzoylmethane, sold under the trademark Eusolex 8020

4-tert-butyl-4'-methoxy-dibenzoylmethane, sold under the trademark Parsol 1789 dianisoylmethane, sold under the trademark Parsol DAM;

certain benzotriazole derivatives such as:

2-(2'-hydroxy-5'-methylphenyl)benzotriazole, sold under the trademark Tinuvin P 2-(2'-hydroxy-5'-tert-octylphenyl)benzotriazole, sold under the trademark Spectra-Sorb UV 5411.

The above list of sunscreens is obviously not restrictive.

At least one of the following compounds is preferably employed as an agent absorbing the UV rays:

2-ethylhexyl p-(dimethylamino)benzoate (Escalot 507)

2-ethylhexyl p-methoxycinnamate (Parsol MCX)

3-benzylidene-d,l-camphor 3-(4'-methylbenzylidene)-d,l-camphor (Eusolex 6300)

amyl 4-(dimethylamino)benzoate (Escalol 506)

homomenthyl salicylate (Filtrasol A)

2-hydroxy-4-methoxybenzophenone (Uvinul M 40 - SpectraSorb UV 9)

N-(2-ethylhexyl)-4-(3'-methylidenecamphor)benzene sulphonamide

N-(2-ethylhexyl)-3-benzylidene-10-camphor sulphonamide, optionally in combination with one of the following compounds:

tert-butyl-4-methoxy-4'-dibenzoylmethane (Parsol 1789)

4-isopropyldibenzoylmethane (Eusolex 8020)

α-(2-oxo-3-bornylidene)toluene-4-sulphonic acid and its salts

α-(2-oxo-3-bornylidene)-p-xylene-2-sulphonic acid 2-hydroxy-4-methoxybenzophenone-5-sulphonic acid 4-[(2-oxo-3-bornylidene)methyl]phenyltrimethylammonium methyl sulphate 1,4-di[sulphocamphorylmethylidene]benzene acid, and 2-phenylbenzimidazole-5-sulphonic acid.

Besides the polymer obtained by block polymerization in emulsion and described in EP-A-0,073,529 and the agents absorbing the ultraviolet radiations, the cosmetic screening composition according to the invention can contain cosmetic adjuvants usually employed in a composition of this type.

Among the principal adjuvants which can be present in a composition of this kind, there may be mentioned solvents such as water, lower monoalcohols or polyalcohols containing from 1 to 6 carbon atoms, or mixtures thereof; there may also be mentioned fatty substances such as oils or mineral, animal or plant waxes, fatty acids, fatty acid esters such as triglycerides of fatty acids containing from 6 to 12 carbon atoms, fatty alcohols and oxyethylenated fatty alcohols.

The mono- or polyalcohols which are more especially preferred are chosen from ethanol, isopropanol, propylene glycol, glycerol and sorbitol.

As fatty substances, among the mineral oils there may be mentioned paraffin oil; among the animal oils, whale, seal, alosa, halibut liver, cod, tuna, turtle, tallow neat's-foot, horse's hoof, sheep's foot, mink, otter, marmot oils and the like; among the plant oils, almond, peanut, wheatgerm, olive, maize germ, jojoba, sesame, sunflower, palm, nut oils, and similar oils.

Among the fatty acid esters, mention can be made of the isopropyl esters of myristic, palmitic and stearic acids and the fatty esters which are solid at 25° C.

Vaseline, paraffin, lanolin, hydrogenated lanolin, acetylated lanolin and silicone oil can also be mentioned as fatty substances.

Among the waxes, there may be mentioned Sipol wax, lanolin wax, beeswax, candelilla wax, microcrystalline wax, carnauba wax, spermaceti, cocoa butter, karite butter, silicone waxes, hydrogenated oils which are solid at 25° C., sucroglycerides, and Ca, Mg, Zr and Al oleates, myristates, linoleates and stearates.

Among the fatty alcohols there may be mentioned lauryl, cetyl, myristyl, stearyl, palmityl and oleyl alcohols, and among the polyoxyethylenated fatty alcohols, lauryl, cetyl, stearyl and oleyl alcohols containing from 2 to 20 moles of ethylene oxide.

The cosmetic composition can also contain emulsifiers which can be nonionic, anionic, cationic or amphoteric.

It may also be useful to use thickeners such as cellulose derivatives, polyacrylic acid derivatives, or guar or carob gums.

The cosmetic composition according to the invention can also contain adjuvants usually employed in cosmetics and especially hydrating products, emollients, dyes, preserving agents and perfumes.

The cosmetic screening composition according to the invention may be presented in the form of an emulsion (cream or milk), a salve, a gel, or be packaged as an aerosol, and in general, in any of the usual forms of the antiactinic cosmetic compositions.

The invention will be illustrated better with the aid of the following nonrestrictive examples:

EXAMPLE 1

| EMULSION (sunscreen cream) | |
|---|---|
| Polymer sold in aqueous emulsion at a concentration of 40% AS under the name Ropaque OP 42 by the company Rohm & Haas | 2.0 g AS |
| 2-ethylhexyl 4-(dimethylamino)benzoate | 2.5 g AS |
| 2-hydroxy-4-methoxybenzophenone | 1.0 g AS |
| Mixture of glycerol mono- and distearate, not self-emulsifiable, sold under the name of Geleol Copeaux by the company Gattefosse | 2.0 g AS |
| Mixture of cetylstearyl alcohol and of cetylstearyl alcohol oxyethylenated with 33 moles of ethylene oxide, sold under the name "Sinnowax AO" by the company Henkel | 7.0 g AS |
| Cetyl alcohol | 1.5 g AS |
| Silicone oil | 1.5 g |
| Paraffin oil | 15.0 g |
| Glycerine | 20.0 g |
| Perfume preserving agent | q.s. |
| Water | q.s. 100.0 g |

It is found that the emulsion of this example containing the polymer Ropaque OP 42, has a sun protection index equal to 6.5, whereas that of the emulsion which contains only the UV screens consisting of 2-ethylhexyl 4-(dimethylamino)benzoate and 2-hydroxy-4-methoxybenzophenone is equal to 4.7.

EXAMPLE 2

| EMULSION (sunscreen milk) | |
| --- | --- |
| Parsol MCX (2-ethylhexyl p-methoxycinnamate) | 4.0 g |
| Ropaque OP 42 | 3.0 g AS |
| Stearyl alcohol | 2.7 g |
| Isopropyl palmitate | 5.0 g |
| Cetylstearyl alcohol containing 33 moles of ethylene oxide | 2.7 g |
| Preserving agent | q.s. |
| Perfume | q.s. |
| Demineralized water | q.s. 100 g |

EXAMPLE 3

| EMULSION (sunscreen cream) | |
| --- | --- |
| Eusolex 6300 (3-(4'-methylbenzylidene)-d,l-camphor) | 4.0 g |
| Ropaque OP 42 | 3.5 g AS |
| Sipol wax | 7.0 g |
| Glycerol monostearate | 2.0 g |
| Paraffin oil | 15.0 g |
| Silicone oil | 1.5 g |
| Cetyl alcohol | 1.5 g |
| Glycerine | 10.0 g |
| Perfume | q.s. |
| Preserving agent(s) | q.s. |
| Dye(s) | q.s. |
| Water | q.s. 100 g |

EXAMPLE 4

| EMULSION (sunscreen cream) | |
| --- | --- |
| 4-[(2-oxo-3-bornylidene)methyl]phenyltrimethyl-ammonium methyl sulphate prepared according to Examples 1 or 2 of French Patent No. 2,199,971 | 1.0 g |
| Benzylidenecamphor | 2.0 g |
| Ropaque OP 42 | 2.5 g |
| Cetyl alcohol | 1.2 g |
| Self-emulsifiable glycerol monostearate | 7.4 g |
| Sorbitan monostearate polyoxyethylenated with 60 moles of ethylene oxide | 2.7 g |
| Lanolin | 4.0 g |
| Paraffin oil | 30.0 g |
| Perfume | q.s. |
| Preserving agent(s) | q.s. |
| Dye(s) | q.s. |
| Water | q.s. 100 g |

EXAMPLE 5

| EMULSION (sunscreen cream) | |
| --- | --- |
| 4-tert-butyl-4'-methoxydibenzoylmethane (parsol 1789) | 0.5 g |
| 2-Ethylhexyl p-methoxycinnamate (Parsol MCX) | 3.0 g |
| Ropaque OP 42 | 3.0 g AS |
| Mixture of cetylstearyl alcohol and cetylstearyl alcohol oxyethylenated with 33 moles of ethylene oxide, sold under the name "Sinnowax AO" by the company Henkel | 8.0 g |
| Mixture of nonemulsifiable glycerol mono- and distearate, sold under the name Geleol Copeaux by the company Gattefosse | 2.0 g |
| Cetyl alcohol | 2.0 g |

| EMULSION (sunscreen cream) -continued | |
| --- | --- |
| Paraffin oil | 15.0 g |
| Glycerine | 18.0 g |
| Propylene glycol | 2.0 g |
| Perfume, preserving agent | q.s. |
| Water | q.s. 100 g |

EXAMPLE 6

| EMULSION (sunscreen milk) | |
| --- | --- |
| Homomenthyl salicylate | 6.0 g |
| 2-Ethylhexyl p-(dimethylamino)benzoate (Escalol 507) | 1.0 g |
| Ropaque OP 42 | 2.5 g AS |
| Stearyl alcohol | 2.7 g |
| Isopropyl palmitate | 5.0 g |
| Cetylstearyl alcohol containing 33 moles of ethylene oxide | 2.7 g |
| Perfume, preserving agent | q.s. |
| Water | q.s. 100 g |

EXAMPLE 7

| EMULSION (sunscreen cream) | |
| --- | --- |
| N—(2-ethylhexyl)-4-(3'-methylidenecamphor)-benzenesulphonamide | 0.5 g |
| 5-Methyl-2-phenylbenzoxazole (Witisol) | 0.5 g |
| 5-(3,3-Dimethyl-2-norbornylidene)-3-penten-2-one (Prosolal 59) | 3.0 g |
| Ropaque OP 42 | 3.5 g AS |
| Triglycerides of caprylic/capric acid (60/40), sold under the name Miglyol 812 by the company Dynamit Nobel | 20.0 g |
| Mixture of cetylstearyl alcohol and cetylstearyl alcohol containing 33 moles of ethylene oxide, sold under the name "Sinnowax AO" by the company Henkel | 9.0 g |
| Cetyl alcohol | 3.0 g |
| 70% sorbitol | 8.0 g |
| Preserving agent, perfume | q.s. |
| Water | q.s. 100 g |

I claim:

1. A cosmetic UV-radiation screening composition comprising, in combination, in a cosmetically acceptable medium (1) an aqueous dispersion of particles of a water-insoluble acrylic heteropolymer so as to increase the protection index of a UV-radiation screening agent said comprising (a) an ionic polymer forming a core, said ionic polymer containing ionizable acid groups which make the core capable of being swollen by at least partial neutralization with a volatile base selected from the group consisting of ammonia and a lower aliphatic amine and (b) a polymer forming a sheath at least partially encapsulating said core, said sheath being permeable to said volatile base and having a glass transition temperature below 50° C., and said particles being film-forming and being obtained by block polymerization in emulsion and (2) at least one oil-soluble or water-soluble UV-radiation screening agent.

2. The cosmetic UV-radiation screening composition of claim 1 wherein said sheath polymer has a glass transition temperature of −40° C. to 23° C. and encapsulates said core polymer to an extent over 50 percent and said volatile base is present in an amount sufficient to provide a pH of at least 6.

3. The cosmetic UV-radiation screening composition of claim 1 wherein said core polymer comprises the polymerizate of (1) acrylic acid, methacrylic acid or a mixture thereof in an amount of at least 15 percent thereof and (2) a polyunsaturated crosslinking agent in an amount of 0.1 to 3 percent thereof, and wherein said sheath contains not more than 10 percent acrylic acid, methacrylic acid or a mixture thereof and the amount of said acrylic acid, methacrylic acid or a mixture thereof is less than one third that present in said core, the size of said particles before swelling by neutralization being between 0.07 and 4.5 microns.

4. The cosmetic UV-radiation screening composition of claim 1 wherein said water-insoluble acrylic heteropolymer is present in an amount ranging from 0.1 to 10 percent by weight thereof.

5. The cosmetic UV-radiation screening composition of claim 1 wherein said water-insoluble acrylic heteropolymer is present in an amount ranging from 0.5 to 5 percent by weight thereof.

6. The cosmetic UV-radiation screening composition of claim 1 wherein said UV-radiation screening agent is present in an amount ranging from 1 to 20 weight percent thereof.

7. The cosmetic UV-radiation screening composition of claim 1 wherein said UV-radiation screening agent is present in an amount ranging from 2 to 15 weight percent thereof.

8. The cosmetic UV-radiation screening composition of claim 1 wherein said UV-radiation screening agent is selected from the group consisting of (1) a benzylidene camphor, or a derivative thereof (2) p-aminobenzoic acid or a derivative thereof, (3) an anthranilate, (4) a cinnamate, (5) a salicylate, (6) a benzoxazole, (7) 5-(3,3-dimethyl-2-norbornylidene)-3-penten-2-one, (8) ethyl urocanate, (9) the trioleate of 3,4-dihydroxy-[(3,4,5,-trihydroxybenzoyl)-oxy]benzoic acid, (10) sodium 3,4-dimethoxyphenyl glyoxalate, (11) 2- phenylbenzimidazole-5-sulphonic acid or a salt thereof, (12) benzophenone or a derivative thereof, (13) dibenzoylmethane or a derivative thereof and (14) benzotriazole or a derivative thereof.

9. The cosmetic UV-radiation screening composition of claim 1 wherein said UV-radiation screening agent is selected from the group consisting of
2-ethylhexyl p-(dimethylamino) benzoate,
2-ethylhexyl p-methoxy cinnamate,
3-benzylidene-d,l-camphor,
3-(4'-methylbenzylidene)-d,l-camphor,
amyl 4-(dimethylamino) benzoate,
homomenthyl salicylate,
2-hydroxy-4-methoxybenzophenone,
N-(2-ethylhexyl)-4-(3'-methylidene camphor) benzene sulphonamide, and
N-(2-ethylhexyl)-3-benzylidene-10-camphor sulphonamide.

10. The cosmetic UV-radiation screening composition of claim 9 which also includes at least one compound selected from the group consisting of
tert. butyl-4-methoxy-4'-dibenzoylmethane,
4-isopropyldibenzoylmethane,
α-(2-oxo-3-bornylidene) toluene-4-sulphonic acid or a salt thereof,
α-(2-oxo-3-bornylidene)-p-xylene-2-sulphonic acid,
2-hydroxy-4-methoxybenzophenone-5-sulphonic acid,
4-[(2-oxo-3-bornylidene)methyl]phenyltrimethylammonium methyl sulphate,
1,4-di[sulphocamphorylmethylidene]benzene acid and
2-phenylbenzimidazole-5-sulphonic acid.

11. The cosmetic UV-radiation screening composition of claim 1 which also includes at least one adjuvant selected from the group consisting of
a solvent selected from the group consisting of water, a monoalcohol containing 1-6 carbon atoms, a polyalcohol containing 1-6 carbon atoms, or a mixture thereof,
a fatty substance selected from the group consisting of an oil, a mineral wax, an animal wax, a plant wax, a fatty alcohol, an oxyethylenated fatty alcohol, a fatty acid and a fatty acid ester,
a hydrating agent,
a thickener,
an emollient,
a dye,
a preservative,
a perfume and
a propellant.

12. The cosmetic UV-radiation screening composition of claim 1 in the form of an emulsion, a salve, or gel or an aerosol.

13. In a cosmetic UV-radiation screening composition containing at least one oil-soluble or water-soluble UV-radiation screening agent, wherein the improvement comprises combining said UV-radiation screening agent with an aqueous dispersion of particles of a water-insoluble acrylic heteropolymer so as to increase the protection index of UV-radiation screening agent, said heteropolymer comprising (a) an ionic polymer forming a core, said ionic polymer containing ionizable acid groups which make the core capable of being swollen by at least partial neutralization with a volatile base selected from the group consisting of ammonia and a lower aliphatic amine and (b) a polymer forming a sheath at least partially encapsulating said core, said sheath being permeable to said volatile base and having a glass transition temperature below 50° C., said particles being film-forming and being obtained by block polymerization in emulsion.

14. A cosmetic UV-radiation screening composition comprising, in combination, in a cosmetically acceptable medium (1) an aqueous dispersion of water-insoluble acrylic heterpolymer so as to increase the protection index of UV-radiation screening agent, said heteropolymer comprising film-forming core/sheath polymer particles having (i) a core polymerized from (a) an acrylic acid, a methacrylic acid or a mixture thereof, in an amount of at least 15 weight percent and (b) a polyunsaturated crosslinking monomer selected from the group consisting of ethylene glycol diacrylate, ethylene glycol dimethacrylate allyl acrylate, allyl methacrylate 1,3-butanediol diacrylate, 1,3-butanediol dimethacrylate, diethylene glycol diacrylate, diethylene glycol dimethacrylate, trimethylolpropane trimethacrylate and divinylbenzene in an amount of 0.1 to 3 percent relative to the total weight of core monomers, and (ii) a sheath polymer said sheath polymer (i') having a glass transition temperature below 50° C., (ii') encapsulating said core polymer to an extent of over 50 percent thereof and (iii') being permeable to a volatile base selected from the group consisting of ammonia and a lower aliphatic amine and (2) at least one oil-soluble or water-soluble UV-radiation screening agent.

15. A process for protecting human epidermis against UV-radiation comprising applying to said human epidermis a protective amount of the cosmetic UV-radiation screening composition of claim 1.

* * * * *